United States Patent
Mäki-Ikola et al.

(10) Patent No.: US 6,335,372 B1
(45) Date of Patent: Jan. 1, 2002

(54) TREATMENT OF OBSESSIVE COMPULSIVE DISORDER

(75) Inventors: Outi Mäki-Ikola, Turku; Matti Wallin, Espoo; Juha Rouru, Turku; Leena Lehtonen, Helsinki; Martti Jaskari, Martinniemi, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/722,263

(22) Filed: Nov. 28, 2000

(51) Int. Cl.[7] ............................................. A61K 31/135
(52) U.S. Cl. ...................................... 514/646; 514/650
(58) Field of Search .................................. 514/646, 650

(56) References Cited

U.S. PATENT DOCUMENTS 5,652,270 A 7/1997 Budai et al.

OTHER PUBLICATIONS

Bojiti et al., "Pharmacokinetics of deramciclane in dogs", Pharmaceutical Sciences, vol. 3, pp. 503–506 (1997).
Csala et al., "Decrease of gluconeogenesis by deramciclane is counteracted by cytochrome P450 inhibitors", Pharmaceutical sciences, vol. 3, pp. 469–472 (1997).
Hazai et al., "Whole–body autoradiography and quantitative organ–level distribution study of deramciclane in rats", Journal and Pharmacology, vol. 51, pp. 165–174 (1999).
Kanerva H., "Pharmacokinetic studies on deramciclane", Kuopio, Department of Pharmaceutics, University of Kuopio (1999).
Kanerva et al., "Pharmacokinetic of deramciclane in dogs after single oral and intravenous closing and multiple oral dosing", Biopharmaceutics and Drug Disposition, vol. 19, pp. 531–539 (1998).
Kanerva et al., "Pharmacokinetics and safety of deramciclane during multiple dosing", Int. J. Pharmacol Ther., vol. 37 (12), pp. 589–597 (1999).
Kanerva et al., "Different absorption profiles of deramciclane in man and in dog", Journal of Pharmacy and Pharmacology, vol. 50, pp. 1087–1093 (1998).
Kanerva et al., "Brain 5–HT2A receptor occupancy of deramciclane in humans after a single oral administration—a positron emission tomography study", Psychopharmacology, vol. 145. pp. 76–81 (1999).
Klebovich et al., "Comparative pharmacokinetics of deramciclane in rat, dog, rabbit and man after the administration of a single oral dose of 3 mg kg–1", Pharm Pharmacol Commun., vol. 4, pp. 129–136 (1998).
Lengyel et al., "Pharmacokinetics of deramciclane in rabbits", Arzneimittel–Forschung, vol. 48 (II), pp. 1063–1068 (1998).
Lengyel et al., "Absorption of the new anxiolytic compound deramciclane in rats, dogs, and rabbits", Arzneimittel–Forschung, vol. 48 (I), pp. 455–460 (1998).

Magyar et al., "Distribution of deramciclane (EGIS–3886) in rat brain regions", European Journal of Drug Metabolism and Pharmacokinetics, vol. 23 (2), pp. 125–131 (1998).
Nemes et al., "Oral, intraperitoneal and intravenous pharmacokinetics of deramciclane and its N–desmethyl metabolite in the rat", Journal of Pharmacy and Pharmacology, vol. 52 (1), pp. 47–51 (2000).
Visy et al., "Plasma protein binding of deramciclane in different species", Pharmaceutical Sciences, vol. 2, pp. 315–318 (1996).
Visy et al., "Covalent protein binding of a minor deramciclane metabolite in dog plasma" Pharmaceutical and pharmacological commun., vol. 4, pp. 587–590 (1998).
Bilkei–Gorzo et al., "mCPP–induced anxiety in the light –dark box in rats—a new method for screening anxiolytic activity", Psychopharmacology (Berl), vol. 136, pp. 291–298 (1998).
Borden et al., "Cloning of the human homologue of the GABA transporter GAT–3 and identification of a novel inhibitor with selectivity for this site", Receptors and channels, vol. 2, pp. 207–213 (1994).
Détári et al., "Differential EEG effects of the anxiolytic drugs, deramciclane (EGIS–3886), ritanserin and chlordiazepoxide in rats", Psychopharmacology, vol. 142, pp. 318–326 (1999).
Gacsályl et al., "Different antagonist activity of deramciclane (EGIS–3886) on peripheral and central 5–HT2 receptors", Pharmaceutical and pharmacological letters, vol. 6 pp. 82–85 (1996).
Gacsályl et al., "Psychopharmacology of a new anxiolytic agent Egyt–3886", Pharmacological research communications, vol. 20 (1), pp. 115–116 (1988).
Gacsályl et al., "Receptor binding profile and anxiolytic –type activity of deramciclane (EGIS–3886) in animal models", Drug development research, vol. 40, pp. 333–348 (1997).

(List continued on next page.)

Primary Examiner—William R. A. Jarvis
(74) Attorney, Agent, or Firm—Finnegan, Henderson, Farabow, Garrett & Dunner, L.L.P.

(57) ABSTRACT

A method for the treatment of OCD in a mammal by administering to the mammal an effective amount of 1,7,7-trimethylbicyclo[2.2.1]heptane derivative of Formula I

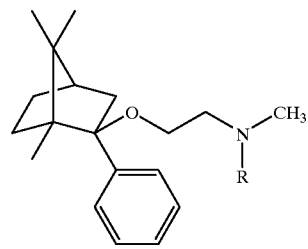

wherein R is hydrogen or methyl, or a pharmaceutically acceptable salt thereof.

13 Claims, No Drawings

OTHER PUBLICATIONS

Kôks et al., "8–OH–DPAT, but not deramciclane, antagonizes the anxiogenic–like action of paroxetine in an elevated plus–maze", Springer–Verlag (2001).

Kovács et al., "Inhibition of high–affinity synaptosomal uptake of gamma–aminobutyric acid a bicyclo–heptane derivative", Arzneim.–Forsch/Drugs Res., vol. 39 (3), pp. 295–297 (1989).

Kovács et al., "Inhibition of [3H]–D–aspartate relase by deramciclane", European journal of pharmacology, vol. 381, pp. 121–127 (1999).

Kovács et al., "Deramciclane inhibits N–methyl–D–aspartate receptor function", Brain research bulletin, vol. 52 (1), pp. 39–44 (2000).

Pälvimäki et al., "Deramciclane, a putative anxiolytic drug, is a serotonin 5–HT2C receptor inverse agonist but fails to induce 5–HT2C receptor down–regulation", Psychopharmacology, vol. 136, pp. 99–104 (1998).

Varga et al., "Effect of deramciclane, a new 5–HT receptor antagonist, on cholescystokinin–induced changes in rat gastrointestinal function", European journal of pharmacology, vol. 367, pp. 315–323 (1999).

Hazai et al., "Application of TLC–digital autoradiography as a rapid method in pilot study of deramciclane metabolism", Journal of Planar Chromatography, vol. 8, pp. 92–97 (1995).

Klebovich et al., "A sensitive, validated Gas–chromatographic bioanalytical method by nitrogen selective detection of deramciclane in dog plasma", Pharmaceutical sciences, vol. 3, pp. 497–501 (1997).

Klebovich et al., "Isolation and identification of deramciclane metabolities by OPC–(DAR) on–line sample collection combined with MS techniques", Instrumental planar chromatography, Visegrád, Hungary, (1998), Research institute for medical plants.

Klebovich et al., "TLC–DAR for the analysis of biological samples. A newly developed rapid tool for studying drug metabolism", Journal of planar chromatography, vol. 10, pp. 399–405 (1997).

Ladányl et al., "Stereochemistry and enantiomeric purity of a novel anxiolytic agent, deramciclane fumarate", Chirality, vol. 11, pp. 689–693 (1999).

Ladányl et al., "Application of overpressured layer chromatography combined with digital autodiagraphy and mass spectrometry in the study of deramciclane metabolism", Journal of AOAC international, vol. 82 (2), pp. 231–238 (1999).

Nemes et al., "A highly sensitive GC method for the determination of deramciclane and its N–desmethyl metabolite in rat and dog plasma", Methodological surveys in bioanalysis of drugs, vol. 24, pp. 103–104 (1996).

Szammer et al., "Synthesis of deramciclane labelled with radiocarbon in various positions", Journal of labeled compounds and radiopharmaceuticals, vol. 39 (12), pp. 1011–1018 (1997).

Szúnyog et al., "Comparative Bioanalytical study of 3H–deramciclane in dog plasma, using a gas chromatography–nitrogen–selective detection (GC–NPD), a new GC–radiochemical detection (GC–RD) and liquid scintillation method", Chromatographia, vol. 48 (1/2), pp. 133–139 (1998).

Szúnyog et al., "A new tool in planar chromatography: combination of OPLC and DAR for fast separation and detecton of metabolites in biological samples", Journal of planar chromatography, vol. 11, pp. 25–29 (1998).

Takács–Novák, "Potentiometric pKa determination of water–insoluble compounds: validation study in methanol/water mixtures", International journal of pharmaceuticals, vol. 151, pp. 235–248 (1997).

Takács–Novák, "A deramciklán (EGIS–3886), agy ú anxiolitikum fizikai–kémiai tulajdonságainak vizsgálata. Ionizátició és lipofilitás", Acta pharmaceutica hungarica, vol. 69, pp. 123–127 (1999).

Tolokán et al., "Determination of deramciclane and N–desmethylderamciclane in human plasma by liquid chromatography–tandem mass spectrometry using off–line robotic sample pretreatment", Journal of chromatography, vol. 896, pp. 279–290 (2000).

Kanerva et al., "The Single Dose Pharmacokinetics and Safety of Dermaciclane in Healthy Male Volunteers", Biopharm. Drug Dispos., vol. 20, pp. 327–334 (1999).

Giral et al., "Reversal of Helpless Behavior in Rats by Putative 5–HT $_{1A}$ Agonists", Biol. Psychiatry, vol. 23, pp. 237–242 (1988).

Armer, "Inhibitors of Mammalian Central Nervous System Selective Amino Acid Transporters", Current Medicinal Chemistry, vol. 7, pp. 199–209 (2000).

EGYT–3886, "Drugs of the Future", vol. 15, pp. 1174–1175 (1990).

TREATMENT OF OBSESSIVE COMPULSIVE DISORDER

FIELD OF THE INVENTION

The present invention relates in general to a method for the treatment of obsessive compulsive disorder in a mammal. More particularly, this invention relates to a method for the treatment of obsessive compulsive disorder in a mammal by administering to the mammal an effective amount of 1,7,7-trimethylbicyclo[2.2.1]heptane derivative of Formula I

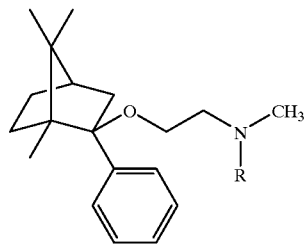

wherein R is hydrogen or methyl, or a pharmaceutically acceptable salt thereof.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BACKGROUND OF THE INVENTION

Obsessive Compulsive Disorder (OCD) is a chronic condition associated with obsessional and compulsive features, such as repetitive compulsive behaviour performed in a ritualistic manner and/or recurrent, intrusive, obsessional thoughts. A patient may suffer from OCD as a single disorder, or OCD may be accompanied by an affective disorder, such as depression or other anxiety disorders, such as Generalized Anxiety Disorder (GAD), Social Anxiety Disorder (SAD), Panic Disorder (PD) or agarophobia.

The active ingredients of this invention, (1R,2S,4R)-(−)-2-phenyl 2-(dimethylaminoethoxy)-1,7,7-trimethyl-bicyclo[2.2.1]heptane, known as deramciclane, and (1R,2S,4R)-(−)-2-phenyl-2-(methylaminoethoxy)-1,7,7-trimethyl-bicyclo[2.2.1]heptane, and their pharmaceutically acceptable acid addition salts with inorganic and organic acids generally used for the purpose, fall within the disclosures of U.S. Pat. No. 4,342,762 and International Patent Application No. WO 98/17230, respectively, which are both incorporated herein by reference.

These compounds are selective serotonin 5HT2A- and/or 5HT2C-receptor antagonists. They have shown anxiolytic-like effects in animal test models.

DESCRIPTION OF THE INVENTION

Applicants have surprisingly discovered that the compounds of formula (I) do reduce one or several symptoms of OCD in a mammal. Accordingly, an object of the present invention is a method for treating OCD in a mammal by administering to the mammal an effective amount of a compound of Formula (I) or a pharmaceutically acceptable salt thereof. Another object of the invention is a method for treating OCD in a mammal by administering to the mammal an effective amount of a compound of Formula (I) or a pharmaceutically acceptable salt thereof together with a benzodiazepine or an antidepressant. The antidepressant may be a tricyclic antidepressant, such as clomipramine, a SSRI, such as fluoxetine or paroxetine, or a SNRI, such as venlafaxine.

For the purposes of this disclosure and claims the term "treatment" is relating to treatment in order to cure or alleviate the disease or its symptoms, and to treatment in order to prevent the development or the exacerbation of the disease or its symptoms.

Pharmaceutically acceptable salts of the compound of Formula (I) can be formed with inorganic acids, e.g. hydrohalogenic acid such as hydrochloride acid or hydrobromic acid, sulfuric acid, phosphoric acid or nitric acid, or organic acids e.g., tartaric acid, succinic acid, malic acid, maleic acid, fumaric acid, citric acid, or lactic acid. Salt with fumaric acid is preferred.

Pharmaceutical compositions containing a compound of Formula (I) or a pharmaceutically acceptable salt thereof as the active ingredient include the usual oral dosage forms, such as tablets, capsules, and liquid preparations. In oral dosage forms, the active ingredient can be mixed with suitable pharmaceutically acceptable excipients, such as starch, lactose, sucrose and magnesium stearate, in accordance with conventional pharmaceutical practice.

The precise amount of the drug to be administered to a mammal for treating or preventing OCD is dependent on numerous factors known to one skilled in the art, such as the compound to be administered, the general condition of the patient, the condition to be treated etc. For example, the usual recommended oral daily dose of deramciclane would be about 5–150 mg, preferably 30–60 mg.

The invention will be further clarified by the following example, which is intended to be purely exemplary of the invention.

EXAMPLE

The efficacy of deramciclane in the treatment of OCD, is illustrated with two patients having obsessive-compulsive symptoms. These patients received one 15 mg tablet of deramciclane twice daily (=30 mg/day) for an eight-week active treatment period.

RESULTS

As assessed by the responsible physician, the obsessive-compulsive symptoms were reduced in a clinically significant way during the 8 week treatment period.

Although the invention has been illustrated by the preceding example, it is not to be construed as being limited to the materials employed therein. Rather, the invention is directed to the generic area as herein disclosed. Various modifications and embodiments thereof can be made without departing from the spirit or scope thereof.

What is claimed is:

1. A method of treating obsessive compulsive disorder in a mammal comprising administering to said mammal an effective amount of a compound of Formula (I)

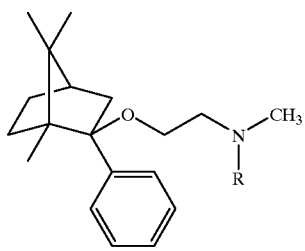

wherein R is hydrogen or methyl, or a pharmaceutically acceptable salt thereof.

2. The method of claim 1, wherein the obsessive compulsive disorder is accompanied with an anxiety disorder.

3. The method of claim 2, wherein the anxiety disorder is Generalized Anxiety Disorder.

4. The method of claim 2, wherein the anxiety disorder is Social Anxiety Disorder.

5. The method of claim 2, wherein the anxiety disorder is Panic Disorder.

6. The method of claim 2, wherein the anxiety disorder is agarophobia.

7. The method of claim 1, wherein the mammal is human.

8. The method of claim 1, wherein the compound is deramciclane or a pharmaceutically acceptable salt thereof.

9. The method of claim 1, wherein about 5–150 mg/day of the compound of Formula (I) or pharmaceutically acceptable salt thereof is administered.

10. The method of claim 9, wherein about 10–60 mg/day of the compound of Formula (I) or pharmaceutically acceptable salt thereof is administered.

11. The method of claim 10, wherein about 30 mg/day of the compound of Formula (I) or pharmaceutically acceptable salt thereof is administered.

12. The method of claim 1, further comprising administering a benzodiazepine together with the compound of Formula (I) or pharmaceutically acceptable salt thereof.

13. The method of claim 1, further comprising administering an antidepressant together with the compound of Formula (I) or pharmaceutically acceptable salt thereof.

* * * * *